United States Patent [19]

Kaeser

[11] Patent Number: 5,321,865
[45] Date of Patent: Jun. 21, 1994

[54] ORAL HYGIENE DEVICE

[75] Inventor: Charles Kaeser, Savigny, Switzerland

[73] Assignee: Trisa Burstenfabrik AG Triengen, Switzerland

[21] Appl. No.: 83,788

[22] PCT Filed: Feb. 7, 1991

[86] PCT No.: PCT/EP90/00653
 § 371 Date: Sep. 30, 1991
 § 102(e) Date: Sep. 30, 1991

[87] PCT Pub. No.: WO91/11971
 PCT Pub. Date: Aug. 22, 1991

Related U.S. Application Data

[63] Continuation of Ser. No. 768,614, Sep. 30, 1991, abandoned.

[30] Foreign Application Priority Data

Feb. 9, 1990 [CH] Switzerland ............................ 425/90

[51] Int. Cl.[5] .............................................. A61C 17/36
[52] U.S. Cl. ........................................ 15/22.1; 601/162
[58] Field of Search ...................... 15/22.1, 22.2, 22.4, 15/24, 29

[56] References Cited

U.S. PATENT DOCUMENTS

| 3,536,065 | 10/1970 | Moret | 15/22.1 |
| 3,588,936 | 6/1971 | Duve | 15/22.1 |
| 4,146,020 | 3/1979 | Moret et al. | 15/22.1 |
| 4,365,376 | 12/1982 | Oda et al. | 15/22.1 |

Primary Examiner—Edward L. Roberts
Attorney, Agent, or Firm—Davis, Bujold & Streck

[57] ABSTRACT

The oral hygiene device of the invention comprises an interchangeable end and a body (10) extended to take said end. The end may be either a movable one carrying a toothbrush or a fixed one (11) consisting of a nozzle designed to emit a pulsed jet of water generated by a pump fitted in the body (10). The movable end is designed to be given a linear and pivoting alternating movement by a drive mechanism (15) actuated by a motor (16) fitted inside the body (10).

11 Claims, 1 Drawing Sheet

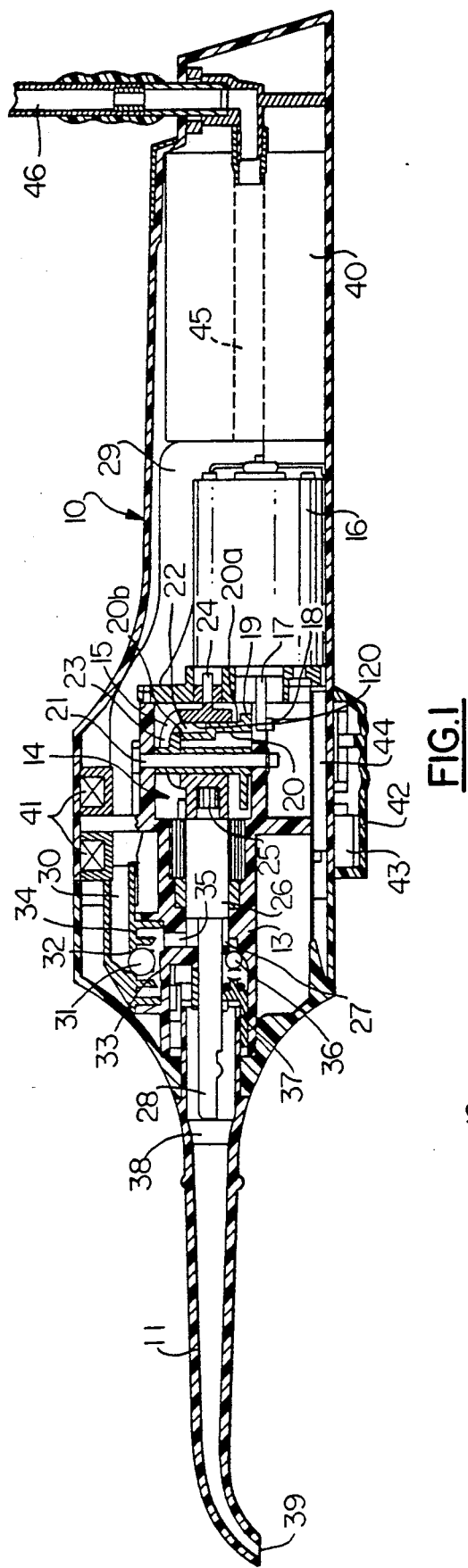
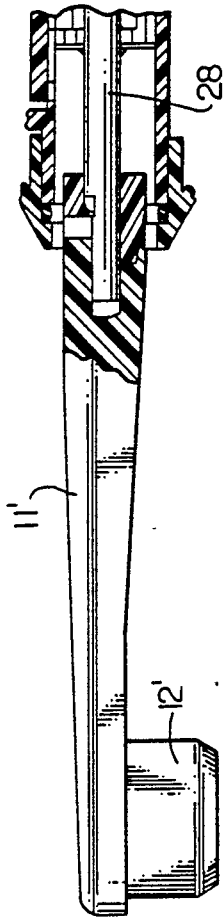
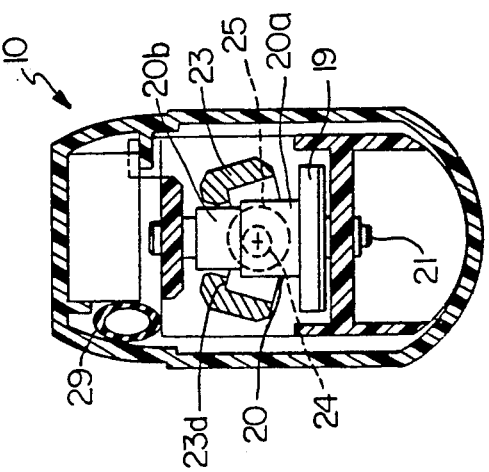
FIG.1
FIG.2
FIG.3

ORAL HYGIENE DEVICE

This is a continuation of copending application Ser. No. 07/768,614 filed on Sep. 30, 1991 now abandoned.

The present invention concerns an oral hygiene device with at least one toothbrush attached to an interchangeable end piece and an elongate body designed to hold said end piece, said body having devices attached to one of its extremities to hold either a first movable end piece with a brush and designed to be given alternate linear movement and alternate pivoting movement around its spindle by a drive mechanism actuated by a motor, or a second fixed end piece consisting of a nozzle.

So-called electric toothbrushes already exist, comprising a body housing a small electric motor driving a mechanism designed to transform the circular movement of the motor spindle into a back and forth motion applied to the brush itself. This movement generally has a very small amplitude, of the order of 1 mm. Due to the fact that the bristles constituting the brush are flexible and because of the small amplitude of movement, the active portion of the brush, that is the ends of the bristles on the brush, vibrate but are not displaced. Therefore, brushing hardly takes place.

These devices are usually supplied with electricity at low voltage through a cord connected to a transformer connected to an electrical socket, which is a bothersome constraint for the user, especially when it is being moved.

In addition to these devices there exist pulsating stream devices designed to emit a stream of highly pressurized water for final rinsing of the teeth and massaging the gums.

The present invention proposes combining these two devices by achieving an oral hygiene device which both cleans and massages by alternately brushing the teeth and gums and by emitting a pulsating stream. These different possibilities impart a universal quality to the device, as it performs all the functions necessary for good dental hygiene.

To achieve this, the device according to the invention is characterized in that the mechanism and the motor are housed inside said body and in that said nozzle is designed to emit a pulsating stream of water generated by a pump also housed inside said body.

According to a preferred embodiment, said pump comprises an alternating displacement piston actuated by said drive mechanism and is designed to emit one stream of pressurized water for each cycle of said drive mechanism.

The drive mechanism preferably comprises one eccentric device and one cam, said eccentric device engaging in a cavity disposed inside said cam.

According to said preferred embodiment, said cam is designed to be movable in the linear direction and pivotable around the spindle according to which linear movement takes place.

The cam may be integral with the alternating linear displacement piston, said piston being situated in a cylindrical chamber supplied with water by an inlet valve.

Advantageously, the piston has a shaft disposed to receive said movable end piece holding a toothbrush.

In this embodiment, the drive mechanism is disposed to have one course of from 1 to 10 mm. and preferably at least approximately equal to 4 mm.

The extremity of said fixed end piece may be designed to block the anterior extremity of the body and allow the pump to communicate with an axial canal disposed inside said end piece through an outlet valve.

The extremity of said movable end piece may be designed to let a light appear between the body and said end piece extremity to shut off the pump.

According to a particularly advantageous embodiment, the motor is supplied with electricity from batteries which can be recharged with a ferrite receptacle charger.

In a first advantageous embodiment the pump may be supplied with water by means of a flexible conduit connected to a source of water which may or may not be pressurized.

According to a second advantageous embodiment the pump may be supplied with water by means of a reservoir situated in the body of the device.

The present invention will be better understood with reference to the description of one exemplary embodiment and to the attached drawings, in which:

FIG. 1 is an axial cross-section of the device according to the invention equipped with a fixed end piece;

FIG. 2 is an enlarged partial axial cross-section of the end of the body of the device holding a movable end piece; and FIG. 3 is a transverse cross-section showing the drive mechanism.

With reference to FIG. 1, the oral hygiene device as shown in the drawings consists of an elongate body 10, one end of which is provided with a fixed end piece 11 which consists of a hollow nozzle designed to emit a pulsating stream of water. Inside this body there is attached a support 13 made of molded synthetic material which defines a housing 14 in which there is a drive mechanism 15 for a movable end piece 11'. Said mechanism 15, which will be described below, is driven by an electric motor 16 situated in the end of the body opposite that which holds said end piece. Said motor 16 comprises an outlet spindle 17 on which there is mounted a drive pinion 18. This drive pinion engages a toothed gear 19 integral with an eccentric device 20 designed to turn around a fixed spindle 21. Eccentric 20 engages in a central opening 22 inside a cam 23, said cam being integral on one side, with an end piece 24 generally perpendicular to spindle 21 of the eccentric device 20, and on the opposite side, with a projection 25 which is centered on the same axis as end piece 24. Said projection 25 is connected to cylindrical element 26 designed to slide axially and to pivot on its axis inside a housing 27 which is also cylindrical and which constitutes the piston for a pump designed to emit the pulsating stream.

Eccentric device 20 is composed of two elements 20a and 20b respectively, the purpose of which are to set in motion the drive means for the movable end piece and the piston in the pump. Portion 20a of this eccentric is responsible for the alternating linear displacement of cam 23 along the spindle common to end piece 24 and knob 25, and the upper portion 20b of the eccentric is responsible for the alternate pivoting motion of said cam 23 around the same spindle. This mechanism is shown in more detail in FIG. 3. This resultant, simultaneous linear movement and pivoting movement along and around the same spindle, respectively, is transmitted to piston 26 and to a shaft 28 which serves both to guide the piston in its linear and pivoting displacement and to support said movable end piece 11'. It is easy to understand that brush 12, which is supported by said movable end piece 11' actually constituting the brush handle, is axially displaced in combination with pivoting movement around said spindle.

The pump is supplied with water by a conduit 29 terminating in canal 30, the outlet of which may be blocked by ball 31 urged against housing 32 by a spring 33. This ball and the spring, which constitute an inlet valve, are situated in chamber 34 which communicates with a radial canal 35 opening into chamber 27 of piston 26. A second ball 36 associated with a spring 37 constitutes an outlet valve for chamber 27 and allows communication between this chamber and interior canal 38 in fixed end piece 11. This fixed end piece has at its free end a small conduit 39 of narrow cross-section for emitting the pressurized stream for each cycle of the drive mechanism for the pump. Note that in the case where the end piece is fixed, its extremity is not in contact with shaft 28 which is alternately displaced inside canal 38.

In the case where movable end piece 11' is attached to the body, the body is shaped appropriately so it can adapt to shaft 28. Its extremity is shaped so that a clearance is provide between it and the body of the device, the effect of which is to render the pump inoperative. In this embodiment, brush 12' held by the end piece is driven in a linear motion and in a pivoting motion, but the pump does not emit any pulsating stream.

It is conceivable to combine a pulsating stream and a brush in the same device, but such an embodiment would require displacement of the outlet valve at the end of end piece 11' which would have to be provided with an interior canal, and would require blocking the pump shutoff clearance.

The motor is fed by several storage batteries 40 housed in the part of the body at the extremity opposite the end pieces. These batteries are preferably charged by means of an induction charger with ferrite receptacles 41 such as those sold commercially by Philips or other companies and which have an excellent output. The complementary elements of the charger are inside a stand, not shown.

Control is effected by means of a sliding switch 42 containing a permanent magnet 43 which acts on two vials containing magnetically engaged micro switches 44. Three positions are advantageously provided, namely, off and two on positions corresponding to two different function speeds.

Various modifications could be made in the way the components are disposed inside the device, particularly insofar as supplying the pump with water is concerned. It could be supplied by connecting a flexible interior conduit 45 connected to the pump by an exterior conduit 46 coupled to either a movable reservoir or a fixed reservoir, or to a source of flowing water (not shown). The pump could also be supplied by means of a reservoir housed in the body of the device.

I claim:

1. Oral hygiene mouth cleaning device having interchangeable brush and nozzle members and comprising:
    a) a housing
    b) attachment means located at a first extremity of said housing for selectively and releasably holding a first, movable, end piece (11') having a brush (12'), forming said brush member, and a second, fixed, end piece (11) forming said nozzle member,
    c) a driving rod (28) being part of said attachment means and defining a longitudinal axis and adapted for mechanical connection to the first, movable, end piece (11') when attached by said attachment means,
    d) a drive mechanism (15) including motion converting means for interconnecting an electric motor (16) and the driving rod (28) to cause said driving rod to simultaneously oscillate and reciprocate, respectively around and along said longitudinal axis of the driving rod, to provide combined rotational and rectilinear oscillation motion of said brush member, when attached by said attachment means, and
    e) a pump cooperating for receiving water from a water feeding means and for supplying a pressure pulse of water through the second, fixed, end piece (11), when attached to said housing by said attachment means, thereby to emit a stream of pulsating water, wherein
    f) said housing supports said drive mechanism and said pump therein.

2. A device according to claim 1, wherein said pump comprises a piston reciprocably driven by said motion converting means, upon rotation of said motor (16), said piston (26) being housed in a cylinder (27), so as to emit a stream of pressurized water, corresponding to the displacement of the piston in the cylinder, during each cycle of the mechanism.

3. A device according to claim 2, wherein the motion converting means comprises an eccentric device (20) cooperating with a rotatable gear (19) engaging a drive pinion (18) of said motor (16), and a cam member (23) fixed to one end of said piston (26), said eccentric device (20) being rotatable around a spindle (21), defining a further axis normal to said longitudinal axis, by said gear (19), and being located inside a cavity of said cam, the cam being movable with said piston (26) along said longitudinal axis and rotatable about said longitudinal axis.

4. A device according to claim 3, wherein the eccentric device (20) includes a first eccentric portion (20a) for causing rectilinear oscillation of the cam member along said longitudinal axis, and a second eccentric portion (20b) providing a rotational oscillation of said cam member about said longitudinal axis, the driving rod (28) being supported at the opposite end of said piston.

5. A device according to claim 4, wherein the piston has a stroke of from about 1 mm to about 10 mm.

6. A device according to claim 5 wherein said stroke is at least about 4 mm.

7. A device according to claim 2, wherein said cylinder (27) comprises inlet valve means and outlet valve means respectively inserted between the water feeding means, and a water channel (38) for emitting the pressurized water stream at each cycle.

8. A device according to claim 7, wherein the second, fixed, end piece (11) forms, when attached to said housing, said nozzle member and is arranged to seal said first extremity of the housing to allow communication between said outlet valve means of the cylinder and said water channel (38) disposed inside the second end piece.

9. A device according to claim 7, wherein a clearance is located between the first, movable, end piece (11') forming said brush member and the first extremity of the housing upon attachment of the first end piece to said driving rod, said clearance being arranged to prevent emission of a pulsating water stream when the brush member is attached to said driving rod.

10. A device according to claim 7, wherein said water feeding means includes a flexible internal conduit (45) connected between the inlet valve means of the pump and a water source.

11. A device according to claim 1, wherein said motor is energized by a rechargeable battery located within said housing at an end remote from the first extremity, said battery being electrically connected to ferrite receptacles (41) cooperating with an external induction charger for charging the battery.

* * * * *